United States Patent [19]

Maruno et al.

[11] Patent Number: 5,077,132
[45] Date of Patent: Dec. 31, 1991

[54] BIOCOMPATIBLE COMPOSITE MATERIAL AND A METHOD FOR PRODUCING THE SAME

[75] Inventors: Shigeo Maruno, Kani; Seiji Ban; Hisashi Iwata, both of Nagoya; Haruo Ito, Tokyo, all of Japan

[73] Assignee: Shigeo Maruno, Gifu, Japan

[21] Appl. No.: 433,415

[22] Filed: Nov. 7, 1989

Related U.S. Application Data

[63] Continuation of Ser. No. 110,339, Oct. 20, 1987, abandoned.

[30] Foreign Application Priority Data

Oct. 20, 1986 [JP] Japan ............................. 61-247592

[51] Int. Cl.$^5$ ............................................. B32B 9/00
[52] U.S. Cl. .................................... 428/426; 428/688; 424/602; 424/656; 424/682; 427/380; 501/17
[58] Field of Search ........................... 424/215, 228.1; 427/380; 501/17; 428/426, 688

[56] References Cited

U.S. PATENT DOCUMENTS

| | | | |
|---|---|---|---|
| 4,097,935 | 7/1978 | Jarcho | 433/228.1 X |
| 4,149,893 | 4/1979 | Aoki et al. | 433/228.1 X |
| 4,308,064 | 12/1981 | Takami et al. | 433/228.1 X |
| 4,518,430 | 5/1985 | Brown et al. | 433/228.1 X |
| 4,673,355 | 6/1987 | Farris et al. | 433/222.1 X |
| 4,708,652 | 11/1987 | Fujii et al. | 501/17 |
| 4,770,943 | 9/1988 | Hakamatsuka et al. | 427/380 |
| 4,794,023 | 12/1988 | Shimamune et al. | 427/380 |

FOREIGN PATENT DOCUMENTS

| | | |
|---|---|---|
| 2336913 | 7/1977 | European Pat. Off. . |
| 0013864 | 8/1980 | European Pat. Off. . |
| 0154513 | 9/1985 | European Pat. Off. . |
| 0187692 | 7/1986 | European Pat. Off. . |
| 0264917 | 4/1988 | European Pat. Off. . |
| 3306648 | 9/1983 | Fed. Rep. of Germany . |
| 63-31654 | 2/1988 | Japan . |

OTHER PUBLICATIONS

Japanese Patent Gazette, Section CH, Week 8544, 12-1-1-85.
Derwent File Supplier, Derwent Publications Ltd., London, GB, Abstract No. AN-87-060440.
Derwent File Supplier, Derwent Publications Ltd., London, GB, Abstract No. AN-86-208809.
S. Ban et al., "Electrochemical corrosion behaviour of hydroxyapatite-glass-titanium composite"; presented at Biointeractions, Oxford (UK), 21-23 Aug. 1990.
S. Maruno et al., "Micro-observation and characterization of bonding between bone and HA-glass-titanium functionally gradient composite", presented at Biointeractions, Oxford (UK), 21-23 Aug., 1990.
"The Furlong Hydroxyapaptite Ceramic Coated Total Hip Replacement":, Joint Replacement Instrumentation Ltd., 1987.
Pre-lecture Abstract, S. Maruno; et al., Japan Institute of Metals, 10/8/86.

Primary Examiner—Patrick J. Ryan
Attorney, Agent, or Firm—Birch, Stewart, Kolasch & Birch

[57] ABSTRACT

A biocompatible composite material comprising a substrate having a glass-hydroxyapatite ceramic layer disposed thereon, and optionally having an intermediate glass layer between the substrate and the layer. The glass-hydroxyapatite ceramic layer comprises a continuous glass phase having a hydroxyapatite ceramic dispersed therein, said hydroxyapatite ceramic having a calcium/phosphorous molar ratio of 1.50 to 1.75, wherein said hydroxyapatite ceramic is comprised mainly of hydroxyapatite. The surface portion of the layer is in a roughened state having voids and having the hydroxyapatite ceramic exposed. The composite material may be produced by a method comprising applying a blend of a powdery glass with a hydroxyapatite ceramic to the surface of a substrate with or without a glass layer disposed thereon, firing the resulting coated substrate and subjecting the fired coated substrate to an etching action with an acid. The composite material is useful as a bone substitute material for the reconsutrction of bone defects.

14 Claims, 11 Drawing Sheets

FIG. 2(a)    FIG. 2(b)
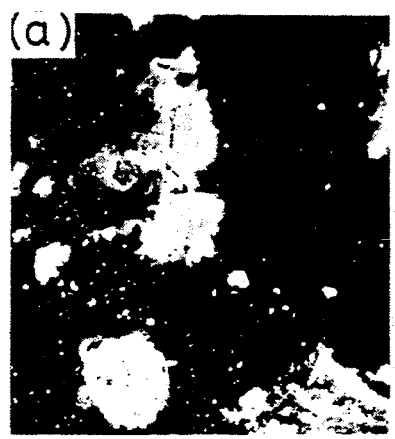 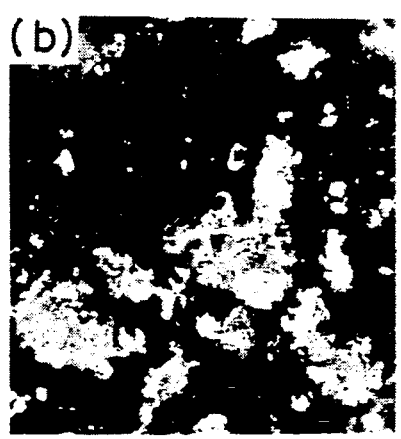
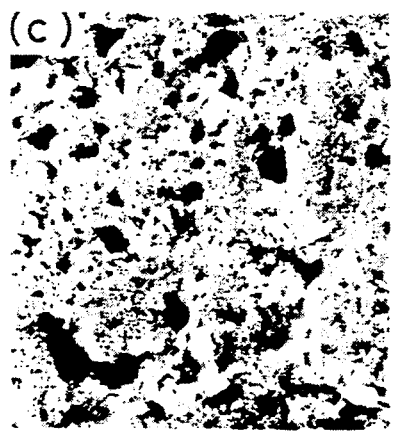 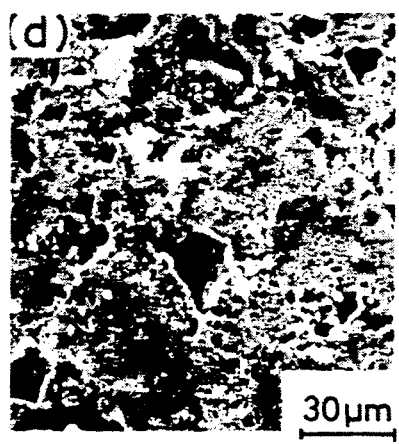
FIG. 2(c)    FIG. 2(d)

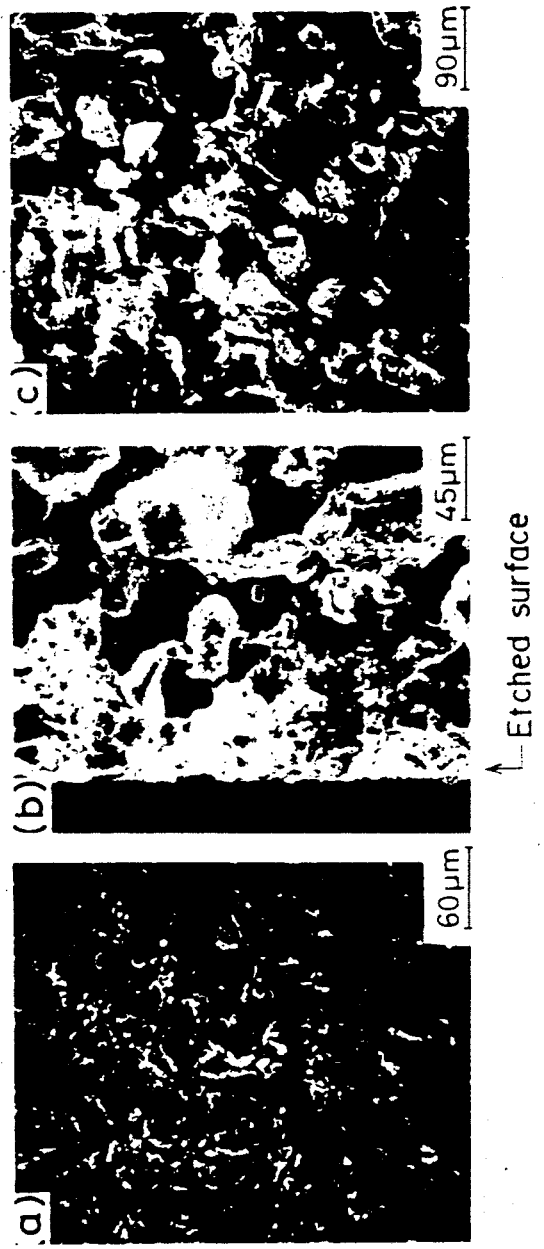
FIG. 3(a) 60μm
FIG. 3(b) 45μm ← Etched surface
FIG. 3(c) 90μm

10 μm

10 μm

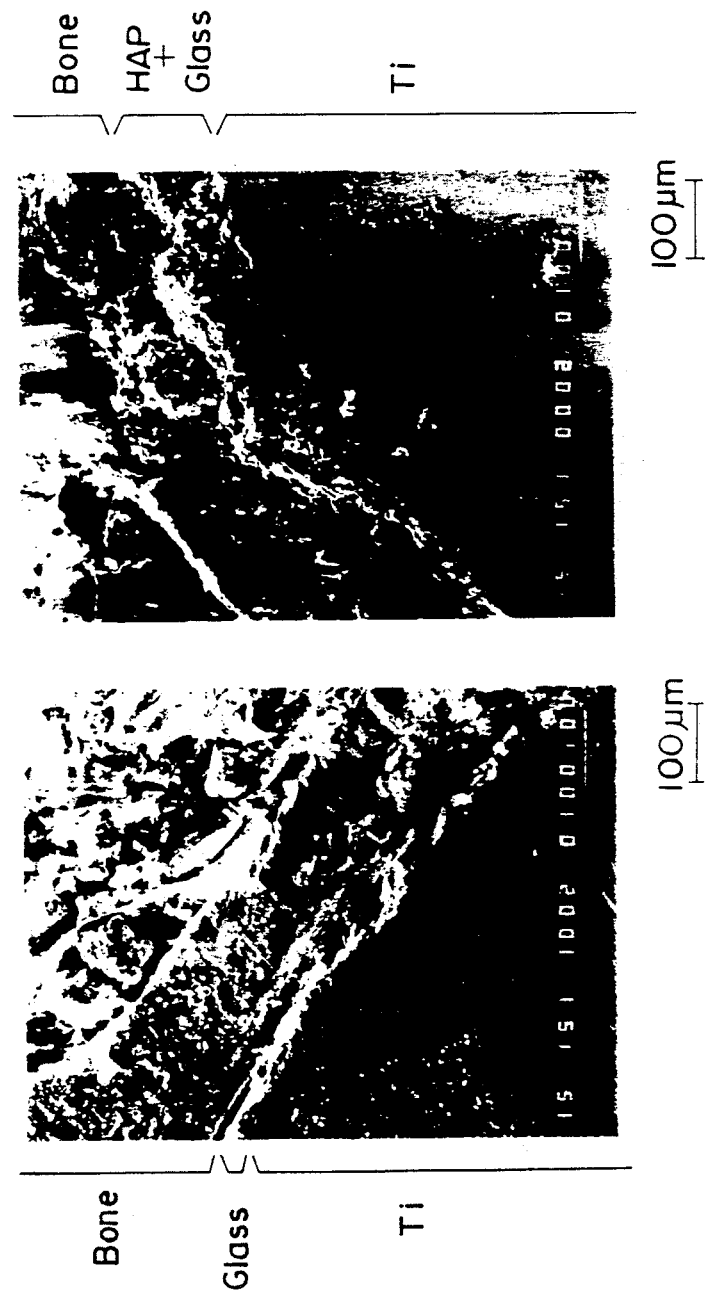

BIOCOMPATIBLE COMPOSITE MATERIAL AND A METHOD FOR PRODUCING THE SAME

This application is a continuation of application Ser. No. 07/110,339 filed on Oct. 20, 1987, now abandoned.

BACKGROUND OF THE INVENTION

1. Field of the Invention

The present invention relates to a biocompatible composite material and a method for producing the same. More particularly, the present invention is concerned with a biocompatible composite material comprising a substrate having a glass-hydroxyapatite ceramic layer disposed thereon, wherein the ceramic layer comprises a continuous glass phase having hydroxyapatite ceramic dispersed therein and wherein the surface portion of said glass-hydroxyapatite ceramic layer is in a roughened state having voids and having the hydroxyapatite ceramic of the glass-hydroxyapatite ceramic layer exposed. The present invention is also concerned with a method for producing the above biocompatible composite material. The biocompatible composite material of the present invention has excellent mechanical strength, is improved with respect to the problem of component dissolution from the material, and has excellent biocompatibility with osseous tissues, exhibiting excellent bioactivities. Therefore, the biocompatible composite material of the present invention is useful as a bioreplacement material such as a bioimplant material. Examples of such replacement materials include those used in the medical field such as an artificial bone, a bone-fixing or coapting material, a bone filler, a bone prosthesis and a partial replacement material for an artificial joint, e.g. joints of hip, elbow and knee, and those used in the dental field such as an artificial root of a tooth, a root canal filler, a bone-fixing or filling material and a material for an artificial tooth.

2. DESCRIPTION OF THE PRIOR ART

In recent years, the art of bioreplacement materials has experienced remarkable progress. In this connection, particular attention is being drawn to the use of ceramic materials which are resistant to chemical actions such as dissolution, corrosion and swelling and are believed to be excellent in biocompatibility with osseous tissues.

In the art, for example, it is known to fabricate an artificial root of a tooth or an artificial bone by shaping hydroxyapatite (hereinafter often referred to as "HAP") into a desired form through sintering the HAP crystallites at a temperature as high as 1000° to 1300° C. without causing decomposition of the crystallites. However, the products thus fabricated are composed mainly of sintered HAP and, therefore, these products, although having a desirable mechanical strength, are very brittle. Further, the shaping of HAP into a desired form with high accuracy by sintering is difficult to perform, which leads to a high production cost. In addition, these products are composed mainly of HAP. Therefore, although these products have an excellent compatibility with osseous tissues, dissolution of HAP tends to occur due to the complicated biochemical reactions in vivo which are caused by the presence of the product in the living body for a prolonged period of time.

Also, it is known to use crystalline sapphire or polycrystalline alumina as a bio-inert, harmless material for an artificial bone, an artificial joint, an artificial root of a tooth or the like. However, the materials used for these products are expensive. Further, in order to implant these materials, it is necessary to form the materials into complicated shapes such as a shape of a screw and to conduct physical implantation into a bone, because these materials do not readily bond directly to the bone. Therefore, this technique has had problems with respect to shaping and to production cost.

Moreover, a method for producing a bioimplant material having a surface layer of HAP has also been proposed. In this method, a coating member having a hollow space is first prepared using a sintered HAP, and then a core is inserted into the hollow space of the coating member. Next, the inner wall of the coating member and the surface of the core are bonded by means of a sintered glass [see, for example, page 138 of pre-lecture publication edited by The Japanese Society for Dental Materials And Devices, Tokyo, Japan (April, 1985)]. This method has the following problems. The preparation of the coating member involves difficult processing of the material into an ultimate shape with a high accuracy of dimension and a high precision in shape. In addition, dissolution of the coating member tends to occur due to the biochemical reactions in vivo over a prolonged period of time, because the coating member is composed only of HAP. Further, the bioimplant article produced according to this method has a structure in which the core and sintered HAP, which are extremely different from each other in linear thermal expansion coefficient ($8.5 \times 10^{-6}$/° C. for a core made of Ti and ten and several times as large as $1 \times 10^{-6}$/° C. for sintered HAP) are bonded together by the use of molten glass. For this reason, a considerable residual strain is produced in the bioimplant article, thereby causing problems of poor thermal shock resistance, poor strength of the sintered HAP and poor adhesion between the sintered HAP and the glass layer. Moreover, since the coating member is prepared by sintering HAP at a high temperature under a high pressure, the surface of the coating member to be contacted with osseous tissues of the living body becomes undesirably smooth. Consequently, the bioimplant material produced according to this method has a poor compatibility with osseous tissues of the living body.

Further, a hip replacement is known in the art, which comprises a substrate and, coated thereon, a surface layer of HAP. In producing this product, the HAP ceramic material is coated on the surface of the substrate by a plasma spraying process. With respect to this product, there are problems that a hip replacement having a thick surface layer of HAP cannot be produced because there is a large difference in linear thermal expansion coefficient between the substrate and HAP, and that the surface of the HAP layer to be contacted with osseous tissues is too smooth for bone to grow into the coated surface.

SUMMARY OF THE INVENTION

The present inventors have made extensive and intensive studies with a view toward developing a biocompatible composite material free from the above-mentioned problems. As a result, the present inventors have unexpectedly found that a composite material comprising a substrate having a glass-hydroxyapatite ceramic layer formed thereon, the surface portion of which is in a roughened state having voids and having the hydroxyapatite ceramic of the glass-hydroxyapatite ceramic layer exposed, has the desired excellent properties. Based on this finding, the present invention has been completed.

Accordingly, it is an object of the present invention to provide a novel biocompatible composite material which has sufficient mechanical strength, is improved with respect to the problem of component dissolution from the material, and has an excellent biocompatibility with osseous tissues, maintaining excellent bioactivities for a prolonged period of time.

It is another object of the present invention to provide a novel method for producing such a novel biocompatible composite material having excellent properties.

The foregoing and other objects, feature and advantages of the present invention will be apparent from the following detailed description taken in connection with the accompanying drawings.

BRIEF DESCRIPTION OF THE DRAWINGS

In the drawings:

FIG. 2 (a) to (d) are SE images showing the surfaces of fired compositions which correspond to the glass-HAP ceramic layer of a composite material of the present invention, which compositions contain various amounts of HAP;

FIG. 3 (a) is an SE image of the etched surface portion of a fired composition which corresponds to a glass-HAP ceramic layer of a composite material of the present invention;

FIG. 3 (b) is an SE image of a cross section of the etched surface portion of a fired composition of FIG. 3 (a), wherein the etching has been conducted for 30 min using 10% hydrogen fluoride (hereinafter often referred to as "HF");

FIG. 3 (c) is an SE image of another cross section of the fired composition of FIGS. 3 (a) and 3 (b), showing the structure in the interior portion of the composition;

FIG. 4 (b) is an SE image of the etched surface portion of the same composition as that of FIG. 4 (a), wherein the etching has been conducted for 3 min using a mixture of 8% HF and 15% $HNO_3$;

FIGS. 5 (b) to (d) are SEM photographs of the etched surface portions of the same layers as the HAP ceramic layer shown in FIG. 5 (a), wherein the etching has been conducted using a mixture (1:1 by volume) of 8% HF and 15% $HNO_3$ for 3 min, 5 min and 10 min, respectively;

FIG. 5 (e) is a magnification (×2.5) of the SEM photograph of FIG. 5 (d);

FIG. 6 (b) is a diagrammatic cross section of a supporting tool used for measuring the pull out strength of a biocompatible composite material;

FIG. 9 (a) is an SE image showing the interface between a composite material comprising a titanium substrate having a glass layer formed thereon and a cortical bone of a pig femur after 2 months from the implantation of the composite material in a pig femur;

FIG. 9 (b) is an SE image showing the interface between a biocompatible composite material of the present invention and a cortical bone of a pig femur after 2 months from the implantation of the composite material in a pig femur;

FIG. 10 (b) is an SE image of a cross section of a system comprising a cancellous bone of a pig femur and, implanted therein, a biocompatible composite material of the present invention after 2 months from the implantation;

FIG. 11 (b) is an magnification of a portion of FIG. 11 (a), which is indicated by an arrow; and FIG. 11 (c) is an SEM photograph of a cross section of the interface between a cortical bone of a dog mandible and a titanium rod after 2 months from the implantation of the titanium rod in a dog mandibular bone.

DETAILED DESCRIPTION OF THE INVENTION

In one aspect of the present invention, there is provided a biocompatible composite material comprising a substrate having a glass-hydroxyapatite ceramic layer disposed thereon, said layer comprising a continuous glass phase having a hydroxyapatite ceramic dispersed therein, said hydroxyapatite ceramic having a calcium/phosphorus molar ratio of 1.50 to 1.75, wherein said hydroxyapatite ceramic is comprised mainly of hydroxyapatite, and wherein the surface portion of said glass-hydroxyapatite ceramic layer is in a roughened state having voids and having the hydroxyapatite ceramic of the glass-hydroxyapatite ceramic layer exposed.

In the biocompatible composite material of the present invention, the surface portion of the glass-hydroxyapatite ceramic layer is in a roughened state so that the surface portion has voids and the hydroxyapatite ceramic of the glass-hydroxyapatite ceramic layer is exposed.

Figure 4A:
FIG. 4 (a) is an SE image of the etched surface portion of the same composition as that of FIG. 3 (a), wherein the etching has been conducted for 3 min using 10% HF.
Figure 4B:

Referring now to FIGS. 3 and 4, there are shown SE (secondary electron) images of fired compositions which correspond to a glass-hydroxyapatite ceramic layer of a composite material of the present invention.

Figures 5A, 5B, 5C, 5D, 5E:
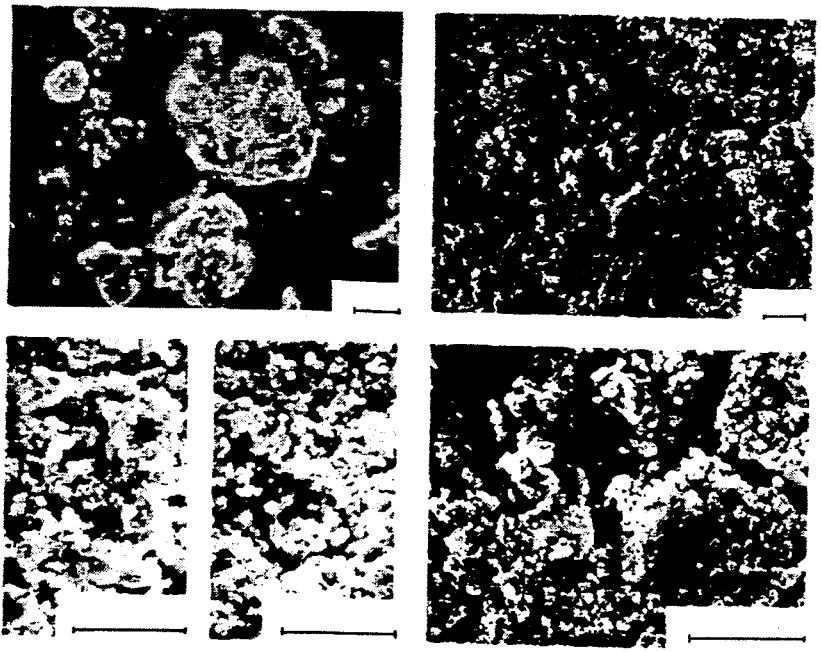
FIG. 5 (a) is a scanning electron microscope (hereinafter referred to as "SEM") photograph of the surface of the glass-HAP ceramic layer of a biocompatible composite material of the present invention before etching.

The hydroxyapatite ceramic is dispersed in the glass-hydroxyapatite ceramic layer. However, the hydroxyapatite ceramic of the layer does not necessarily have a uniform particle diameter throughout the glass-hydroxyapatite ceramic layer but may locally agglomerate so that the hydroxyapatite ceramic is distributed non-uniformly in the layer. As shown in FIG. 3 (b) and (c), the hydroxyapatite ceramic is present in the entire layer of the glass-hydroxyapatite ceramic layer including the surface portion and the interior of the layer. It is preferred that the hydroxyapatite ceramic be concentrated at the surface portion of the layer. Further, as shown in FIG. 3 (b) and (c) and FIG. 4 (b), the glass-hydroxyapatite ceramic layer has a vast plurality of voids and a vast plurality of cracks. From FIG. 5, the presence of a vast plurality of voids having a size of about several microns is confirmed. The void size is in the range as known in the art to be suited for coaptation with an osseous tissue, which is from a few microns to about 500 $\mu$m. It is preferred that the surface portion of the glass-hydroxyapatite layer has a rugged texture in which there are a number of cracks in the order of $\mu$m in width and a vast plurality of voids of several microns in size between particles, as shown in FIG. 5 (b), (c) and (d). This is because such a texture is suitable for the bonding of the composite material to a bone.

The hydroxyapatite ceramic is firmly held by the continuous glass phase. This prevents the hydroxyapatite ceramic from dissolving out into a living body and enables the biocompatible composite material of the present invention to exhibit the desired bioactivities over a prolonged period of time.

In the present invention, the glass-hydroxyapatite ceramic layer may comprise a plurality of sub-layers each comprised of a continuous glass phase having a hydroxyapatite ceramic dispersed therein. The sub-layers have different hydroxyapatite ceramic contents which are increased from the innermost sub-layer toward the outermost sublayer. Alternatively, the glass-hydroxyapatite ceramic layer may comprise at least three sub-layers each comprising a continuous glass phase having a hydroxyapatite ceramic dispersed therein, wherein the sub-layers include at least one combination of at least two mutually adjacent sub-layers of which the hydroxyapatite ceramic contents are identical with each other and have different hydroxyapatite ceramic contents between at least two mutually adjacent sub-layers, in which the hydroxyapatite ceramic contents of the sub-layers constituting the entire glass-hydroxyapatite ceramic layer are increased from the innermost sub-layer toward the outermost sub-layer through at least one sub-layer of which the hydroxyapatite ceramic content is identical with that of a sub-layer immediately preceding said sub-layer. The surface portion of the outermost sub-layer of the glass-hydroxyapatite ceramic layer is in a roughened state having voids and having the hydroxyapatite ceramic of the glass-hydroxyapatite ceramic layer exposed.

Moreover, in the present invention, the composite material according to the present invention may have an intermediate layer between the substrate and the glass-hydroxyapatite ceramic layer wherein said intermediate layer comprises glass and is bonded to each of the opposing surfaces of the substrate and the glass-hydroxyapatite ceramic layer. The presence of the intermediate layer is preferred from the viewpoints of the adhesion between the substrate and the glass-hydroxyapatite ceramic layer and of enabling the content of the hydroxyapatite ceramic in the layer to be increased as explained hereinafter.

The type of a material used for forming the substrate to be used in the present invention is not specifically limited as long as the material has sufficient mechanical strength and chemical resistance and is not only non-toxic to living bodies but also resistant to temperatures at which the latermentioned firing of the substrate having a glass-hydroxyapatite ceramic blend coated thereon is effected. Representative examples of such materials include various types of metals and various types of ceramics. Examples of metals which may be preferably employed in the present invention include titanium; titanium alloys such as Ti-6Al-4V, Ti-6Al-4V+20 vol % Mo, Ti-6Al-4V+40 vol % Mo; Ni—Cr alloys; Co—Cr alloys; and stainless steel. Of these, titanium and titanium alloys are preferred because they have excellent anti-corrosive properties in vivo and have a good compatibility with living bodies. Ti—Al alloys are most preferred because these alloys have high mechanical strength and can be readily fabricated into a substrate having a complicated shape with high precision and high accuracy. Representative examples of employable ceramics include machinable ceramics such as mica glass ceramics ($KMg_3AlSi_3O_{10}F_2$), mechanically strengthened ceramics such as partially stabilized zirconia ($psZrO_2$), and the like.

The metallic substrate may have an oxide layer on its surface. Such a layer will facilitate the bonding between the glass-hydroxyapatite ceramic layer and the metallic substrate. Further, the surface of the metallic substrate may preferably be roughened.

In the case in which the surface is roughened, the average roughness thereof may be preferably 1 to 7 $\mu$m, more preferably 1 to 3.4 $\mu$m. With respect to the average roughness, reference may be made to Japanese Industrial Standard B0601 (1983), pages 9 to 15, and J. Okoshi "Surface Roughness Testing Method", page 22, published by Corona Publishing Co., Japan in 1959.

In the present invention, it is requisite that the hydroxyapatite ceramic have a calcium/phosphorus molar ratio of 1.50 to 1.75. Further, it is preferred that the hydroxyapatite ceramic contain a large amount of HAP which is represented by the formula $Ca_{10}(PO_4)_6(OH)_2$ and has a calcium/phosphorus molar ratio of 1.67. The hydroxyapatite ceramic may contain calcium phosphates such as $Ca_3(PO_4)_2$, $Ca_3(PO_3)_2$ or the like. It is most preferred that the hydroxyapatite ceramic consists solely of HAP. HAP is the main component of the bone of living bodies.

The type of a glass to be employed in the present invention is not limited. Examples of the glass which may suitably be employed to form the above-mentioned glass-hydroxyapatite ceramic layer and glass layer are a borosilicate glass and an aluminosilicate glass. Of the borosilicate glass, an alumina borosilicate glass is most preferred. The alumina borosilicate glass to be used in the present invention preferably contains 75 to 85% by weight of a mixture of $SiO_2$, $B_2O_3$ and $Al_2O_3$, based on the weight of the glass, and from 14 to 20% by weight of at least one metal oxide, preferably at least two different metal oxides, in which the metal of the metal oxide or the metal of each of the different metal oxides is a member selected from the group consisting of alkali metal oxides such as $Na_2O$, $K_2O$ and $Li_2O$ and alkaline earth metal oxides such as CaO. The other component of the alumina borosilicate glass may be at least one member selected from the group consisting of oxides such as $ZrO_2$ and $TiO_2$ and alkaline earth metal compounds such as $CaF_2$ and $Ca_3(PO_4)_2$. In this connection, sitions from the viewpoint of a desired strength of adhesion with the substrate.

TABLE 1

| Sample No. | $SiO_2$ | $Al_2O_3$ | $ZrO_2$ | $TiO_2$ | $Na_2O$ | $K_2O$ | $Li_2O$ | $B_2O_3$ | CaO | $CaF_2$ | $Ca_3(PO_4)_2$ | total |
|---|---|---|---|---|---|---|---|---|---|---|---|---|
| 1 | 67.7 | 5.2 | 1.05 | 1.05 | 8.3 | 4.2 | 2.1 | 10.4 | | | | 100 |
| 2 | 65 | 5 | 1 | 1 | 8 | 4 | 2 | 10 | | | 4 | 100 |
| 3 | 62 | 5.5 | 3.0 | 5.0 | 13.0 | 3.0 | | | 2.5 | 6.0 | | 100 |
| 4 | 60 | 5.0 | 4.0 | 5.0 | 20.0 | | | | | 6.0 | | 100 |
| 5 | 43 | 8 | 5 | | 13 | 6 | 4 | 5 | 9 | 7 | | 100 |
| 6 | 60 | 3 | 4 | 5 | 3 | 3 | 3 | 4 | 9 | 6 | | 100 |
| 7 | 60 | 6 | 4 | | | 20 | | 4 | | 6 | | 100 |
| 8 | 60 | 8 | 4 | | 10 | 10 | 5 | | 3 | | | 100 |

$TiO_2$ is useful in controlling the coloration so that the glass becomes e.g. opaque or white, which is desirable in dental applications and the like. The addition of $ZrO_2$ and $Ca_3(PO_4)_2$ is advantageous from the viewpoint of increasing the mechanical strength of the ultimate glass. The aluminosilicate glass to be used in the present invention preferably contains 60 to 75% by weight of a mixture of $SiO_2$ and $Al_2O_3$, based on the weight of the glass, and from 14 to 20% by weight of at least one metal oxide, in which the metal of the metal oxide is a member selected from the group consisting of alkali metal oxides such as $Na_2O$, $K_2O$ and $Li_2O$ and alkaline earth metal oxides such as CaO. The other component of the aluminosilicate glass may be those as mentioned above with respect to the other component of the alumina borosilicate glass.

When the content of the alkali metal component and/or alkaline earth metal component in the glass exceeds the above-mentioned range, i.e. 14 to 20% by weight, the linear thermal expansion coefficient of the glass becomes too large as compared with that of the substrate. This is undesirable because the strain due to temperature change of the composite material becomes extremely high at the time of firing as mentioned later. In this connection, it is preferred in the present invention that the linear thermal expansion coefficient of the glass be in the range of from 90 to 95% of that of the substrate, taking into consideration the fact that glass is strong to compression stress and weak to pulling stress. Moreover, the excess addition of alkali metal component and/or alkaline earth metal component causes a problem of alkali component dissolution into body fluid, leading to an irritation of the tissues and cells, when the composite material is actually implanted in a human body. Further, the excess use of alkali metal component and/or alkaline earth metal component tends to cause the component to react with HAP, decomposing the same.

On the other hand, when the content of the alkali metal component and/or alkaline earth metal in the glass is too small, i.e. less than 14% by weight, the melt temperature of the glass becomes too high and, it becomes necessary to conduct the formation of the glass-hydroxyapatite layer or the glass layer on the substrate at such a high temperature that the mechanical strength of the substrate is substantially decreased, that the side of the substrate remote from the glass-hydroxyapatite ceramic layer is oxidized to titanium dioxide thereby causing the substrate to become very brittle, and that reaction would occur between the glass component and the hydroxyapatite ceramic.

Examples of glass compositions are shown in the Table 1, in which Nos. 1 to 4 are examples of desirable glass compositions to be used in the present invention and Nos. 5 to 8 as examples of undesirable glass compositions from the viewpoint of a desired strength of adhesion with the substrate.

With respect to the composite material according to the present invention, where a metallic substrate is used as the substrate, it is preferred that the glass of the glass-hydroxyapatite ceramic layer and of the intermediate layer have a linear thermal expansion coefficient corresponding to from about 80 to about 95%, preferably from about 90 to 95% of that of the metallic substrate, from the viewpoint of the desired strength of adhesion between the layer and the substrate.

The linear thermal expansion coefficient of the glass-hydroxyapatite ceramic layer is increased not only by an increase in the coefficient of the glass component itself but also by an increase in the hydroxyapatite ceramic content. Therefore, the linear thermal expansion coefficient of the glass-hydroxyapatite layer can also be controlled by regulating the hydroxyapatite ceramic content. Where a metallic substrate is used as the substrate, it is preferred that the linear thermal expansion coefficient of the glass-hydroxyapatite ceramic layer is about 90 to 100% of that of the metallic substrate.

In the case where there is an intermediate layer of glass formed between the glass-hydroxyapatite ceramic layer and the substrate and a metallic substrate is used as the substrate, it is preferred that the linear thermal expansion coefficient of the glass-hydroxyapatite ceramic layer be between about 90 to 150% of that of the substrate.

Where a ceramic substrate is used as the substrate, the above-mentioned relationships in linear thermal expansion coefficient between the substrate and the materials to be coated thereon can be neglected because the ceramic has not only good affinity for these materials but also is reactive with these materials at the firing temperature, so that a strong bonding is established therebetween.

In the present invention, when the glass-hydroxyapatite ceramic layer is directly formed on the substrate, the hydroxyapatite ceramic content is preferably in the range of from 15 to 50%, more preferably 35 to 50% by weight. In the case of a biocompatible composite material comprising a substrate having a plurality of glass-hydroxyapatite ceramic sub-layers disposed directly thereon, the average hydroxyapatite ceramic content is preferably in the range of from 15 to 50% by weight. On the other hand, when an intermediate glass layer is formed between the glass-hydroxyapatite ceramic layer and the substrate, the hydroxyapatite ceramic content of the glass-hydroxyapatite ceramic layer is preferably 15 to 70%, more preferably 35 to 70% by weight. A hydroxyapatite ceramic content lower than the above-mentioned range is undesirable because the biocompatibility with osseous tissues is adversely affected. The reason why the upper limit of the hydroxyapatite ceramic content is 50% by weight when no intermediate glass layer is employed is that when the content exceeds 50% by weight, the adhesion with the substrate is poor. When an intermediate glass layer is employed, the adhesion with the substrate is improved and the glass-hydroxyapatite ceramic layer and the glass layer are strongly adhered to each other. Even in this case, the hydroxyapatite ceramic content of the glass-hydroxyapatite layer is preferably not larger than 70% by weight. When it exceeds this range, the problem of coming-off of the hydroxyapatite ceramic and dissolution of HAP tends to occur. In the case of a biocompatible composite material comprising a substrate having a plurality of glass-hydroxyapatite ceramic sub-layers disposed thereon through an intermediate glass layer, the average hydroxyapatite ceramic content is preferably in the range of from 15 to 70% by weight.

The biocompatible composite material of the present invention may be advantageously produced by the methods as described below.

Accordingly, in another aspect of the present invention, there is provided a method for producing a biocompatible composite material which comprises the steps of:

(1) applying a blend of a powdery glass with a hydroxyapatite ceramic to the surface of a substrate to form a substrate having the blend disposed thereon, said hydroxyapatite ceramic having a calcium/phosphorus molar ratio of 1.50 to 1.75 and wherein said hydroxyapatite ceramic is comprised mainly of hydroxyapatite, (2) firing the substrate having the blend disposed thereon to obtain a preliminary product comprising a substrate having a glass-hydroxyapatite ceramic layer disposed thereon, said layer comprising a continuous glass phase having a hydroxyapatite ceramic dispersed therein, and (3) subjecting said preliminary product to an etching action with an acid so as to dissolve the glass at the surface portion of the glass-hydroxyapatite ceramic layer remote from the substrate, thereby causing said surface portion to be roughened so that the surface portion has voids and the hydroxyapatite ceramic of the glass-hydroxyapatite ceramic layer is exposed.

In the above method, the sequence of steps (1) and (2) may be repeated prior to step (3), wherein the hydroxyapatite ceramic content of the blend is increased with each repetition of said sequence, wherein the sub-layers have different hydroxyapatite ceramic contents which are increased from the innermost sub-layer toward the outermost sub-layer. Alternatively, the sequence of steps (1) and (2) may be repeated at least two times prior to step (3), wherein the hydroxyapatite ceramic content of the blend is unchanged with at least one repetition of the sequence of steps (1) and (2) while the hydroxyapatite ceramic content of the blend is increased with at least one repetition of the sequence of steps (1) and (2). The glass-hydroxyapatite ceramic layer of the preliminary product thus formed comprises at least three sub-layers each comprising a continuous glass phase having a hydroxyapatite ceramic dispersed therein, wherein the sub-layers include at least one combination of at least two mutually adjacent sub-layers of which the hydroxyapatite ceramic contents are identical with each other and have different hydroxyapatite ceramic contents between at least two mutually adjacent sub-layers, in which the hydroxyapatite ceramic contents of the sub-layers constituting the entire glass-hydroxyapatite ceramic layer are increased from the innermost sub-layer toward the outermost sub-layer through at least one sub-layer of which the hydroxyapatite ceramic content is identical with that of a sub-layer immediately preceding said sub-layer. This is effective for forming a glass-HAP ceramic layer having a uniform dispersion of the HAP ceramic in the glass. These methods are advantageous in that the HAP content of the outermost sub-layer can be increased up to, for example, about 95%. This is advantageous from the viewpoint of the biocompatibility with osseous tissues. In this connection, it is noted that the HAP content of the innermost sub-layer can be as low as about 15% by weight. The average HAP content of the entire glass-HAP ceramic layer is 15 to 50%.

Also, in the above method, a powdery glass may be applied to the surface of the substrate and the resultant may be fired to form a semi-coated substrate having a glass layer disposed thereon prior to step (1) so that there may be obtained a composite material in which a single glass-HAP ceramic layer or a plurality of glass-HAP ceramic sub-layers are formed on a substrate through an intermediate glass layer.

In particular, a biocompatible composite material having the single glass-HAP ceramic layer and having the intermediate layer may be produced by a method which comprises the steps of:

(1) applying a powdery glass to the surface of a substrate to coat the substrate with the powdery glass, (2) firing the powdery glass coated substrate to form a glass coated substrate, (3) applying a blend of a powdery glass with a hydroxyapatite ceramic to the surface of the glass coated substrate to form a glass coated substrate having the blend disposed thereon, said hydroxyapatite ceramic having a calcium/phosphorus molar ratio of 1.50 to 1.75 and wherein said hydroxyapatite ceramic is comprised mainly of hydroxyapatite, (4) firing the glass coated substrate having the blend disposed thereon to obtain a preliminary product comprising a substrate having a glass layer disposed thereon, which in turn has a glass-hydroxyapatite ceramic layer disposed thereon, said layer comprising a continuous glass phase having a hydroxyapatite ceramic dispersed therein, and (5) subjecting said preliminary product to an etching action with an acid so as to dissolve the glass at the surface portion of the glass-hydroxyapatite ceramic layer remote from the substrate, thereby causing said surface portion to be roughened so that the surface portion has voids and the hydroxyapatite ceramic of the glass-hydroxyapatite ceramic layer is exposed.

Further, a biocompatible composite material having the plurality of glass-HAP ceramic sub-layers may be produced by following steps (1) and (2) of the above method and repeating the sequence of steps (3) and (4) prior to step (5), wherein the hydroxyapatite ceramic content of the blend is increased with each repetition of said sequence to obtain a preliminary product comprising a glass-hydroxyapatite ceramic layer which comprises a plurality of sub-layers, each comprising a continuous glass phase having a hydroxyapatite ceramic dispersed therein, said sub-layers having different hydroxyapatite ceramic contents, in which said contents are increased from the innermost sub-layer toward the outermost sub-layer. Alternatively, following steps (1) and (2) of the above method, the sequence of steps (3) and (4) may be repeated at least two times prior to step (5), wherein the hydroxyapatite ceramic content of the blend is unchanged with at least one repetition of the sequence of steps (3) and (4) while the hydroxyapatite ceramic content of the blend is increased with at least one repetition of the sequence of steps (3) and (4), so that the glass-hydroxyapatite ceramic layer of the preliminary product formed comprises at least three sub-layers each comprising a continuous glass phase having a hydroxyapatite ceramic dispersed therein, wherein the sub-layers include at least one combination of at least two mutually adjacent sub-layers of which the hydroxyapatite ceramic contents are identical with each other and have different hydroxyapatite ceramic contents between at least two mutually adjacent sub-layers, in which the hydroxyapatite ceramic contents of the sub-layers constituting the entire glass-hydroxyapatite ceramic layer are increased from the innermost sub-layer toward the outermost sub-layer through at least one sub-layer of which the hydroxyapatite ceramic content is identical with that of a sub-layer immediately preceding said sub-layer. This is effective for forming a glass-HAP ceramic sub-layer having a uniform dispersion of the HAP ceramic in the glass.

Alternatively, the biocompatible composite material having an intermediate glass layer may be produced by a method comprising the steps of:

(1) applying a blend of a powdery glass with a hydroxyapatite ceramic to the glass layer surface of a glass coated substrate comprising a substrate having disposed thereon a glass layer remote from the substrate to form a coated substrate having the applied blend disposed thereon, said hydroxyapatite ceramic having a calcium/phosphorus molar ratio of 1.50 to 1.75 and wherein said hydroxyapatite ceramic is comprised mainly of hydroxyapatite, (2) firing the glass coated substrate having the blend disposed thereon to obtain a preliminary product comprising a substrate having a glass layer disposed thereon, which in turn has a glass-hydroxyapatite ceramic layer disposed thereon, said ceramic layer comprising a continuous glass phase having a hydroxyapatite ceramic dispersed therein, and (3) subjecting said preliminary product to an etching action with an acid so as to dissolve the glass at the surface portion of the glass-hydroxyapatite ceramic layer remote from the substrate, thereby causing said surface portion to be roughened so that the surface portion has voids and the hydroxyapatite ceramic of the glass-hydroxyapatite ceramic layer is exposed.

In the above method, the sequence of steps (1) and (2) may be repeated prior to step (3), wherein the hydroxyapatite ceramic content of the blend is increased with each repetition of said sequence to obtain a preliminary product comprising a glass-hydroxyapatite ceramic layer which comprises a plurality of sub-layers, each comprising a continuous glass phase having a hydroxyapatite ceramic dispersed therein, said sub-layers having different hydroxyapatite ceramic contents, in which said contents are increased from the innermost sub-layer toward the outermost sub-layer. Alternatively, the sequence of steps (1) and (2) of the above method may be repeated at least two times prior to step (3), wherein the hydroxyapatite ceramic content of the blend is unchanged with at least one repetition of the sequence of steps (1) and (2) while the hydroxyapatite ceramic content of the blend is increased with at least one repetition of the sequence of steps (1) and (2). The glass-hydroxyapatite ceramic layer of the preliminary product thus formed comprises at least three sub-layers each comprising a continuous glass phase having a hydroxyapatite ceramic dispersed therein, wherein the sub-layers include at least one combination of at least two mutually adjacent sub-layers of which the hydroxyapatite ceramic contents are identical with each other and have different hydroxyapatite ceramic contents between at least two mutually adjacent sub-layers, in which the hydroxyapatite ceramic contents of the sub-layers constituting the entire glass-hydroxyapatite ceramic layer are increased from the innermost sub-layer toward the outermost sub-layer through at least one sub-layer of which the hydroxyapatite ceramic content is identical with that of a sub-layer immediately preceding said sub-layer. This is effective for forming a glass-HAP ceramic sub-layer having a uniform dispersion of the HAP ceramic in the glass.

It is preferred that the substrate be subjected to blasting. Before blasting, degreasing and pickling may preferably be conducted. The blasting is conducted so that the average roughness becomes 1 to 7 μm, preferably 1 to 3.4 μm. When a metallic substrate is used as the substrate, after the blasting, an oxidative layer may optionally be formed on the surface of the substrate by a heat treatment at 900° to 950° C. under vacuum.

The formation of the glass-hydroxyapatite ceramic layer on the substrate may be conducted as follows.

The hydroxyapatite having a calcium/phosphorus molar ratio of 1.50 to 1.75 and wherein said hydroxyapatite ceramic is comprised mainly of hydroxyapatite is commercially available and can be produced by known methods. With respect to the preparation of the hydroxyapatite ceramic, reference may be made, for example, to T. Fujiu and Ogino; Journal of Biomedical Materials Research, Vol. 18, 845–859 (1984). For example, the HAP ceramic may be produced by a customary wet process. When the wet process is employed, the resulting HAP ceramic, after drying, is preferably subjected to preliminary heating at 800° C. and then to heating at 1200° C., followed by grinding to regulate the particle size.

With respect to the procedure for preparing the glass, reference may be made to, for example, S. Sakka, et al. "Glass Handbook" published by Asakura Shoten K.K., Tokyo, Japan in 1975. The glass is also subjected to grinding.

The HAP particles may be well mixed with the powdery glass, followed by addition of a liquid, e.g. water (e.g. weight ratio: HAP and powdery glass/water=3:1 to 1:5), and the resulting blend may be applied onto the surface of the substrate, followed by drying and firing. The firing temperature is preferably in the range of from 850° to 1150° C. When the firing temperature is less than 850° C., both the mechanical strength of the glass-hydroxyapatite ceramic layer and the adhesion of said layer with the substrate becomes poor. When the firing temperature is more than 1150° C., the substrate (particularly titanium or a titanium alloy) undergoes a decrease in mechanical strength and HAP tends to decompose due to a reaction with the glass component.

The surface of the thus formed glass-hydroxyapatite ceramic layer may be subjected to an etching action with an acid. The etching action may preferably be conducted by the use of a solution of HF and $HNO_3$. Also, the etching action may preferably be conducted by a method in which the surface to be etched is exposed to an acid vapor containing HF atmosphere for a predetermined period of time until an evenly etched surface is obtained.

With respect to the method for producing a composite material which has a glass layer between the glass-hydroxyapatite ceramic layer and the substrate, substantially the same procedure as described above may be conducted except for forming the glass layer. The heating temperature for forming the glass layer is preferably 850° to 1150° C.

By the above mentioned etching action, which mainly acts on the glass, the surface portion of the glass-hydroxyapatite ceramic layer is converted to a roughened state having voids and having the hydroxyapatite ceramic of the glass-hydroxyapatite ceramic layer exposed. The size of the voids is preferably several microns to several tens of microns.

According to the present method, an excellent biocompatible composite material can be readily obtained through simple operations. The method of the present invention has remarkable advantages from a viewpoint of simplicity and production cost, as compared with the conventional methods such as the plasma spraying method.

According to the present invention, the thickness of the glass-hydroxyapatite ceramic layer can be freely increased and controlled. According to usage, the thickness may be about 50 $\mu$m to about 300 $\mu$m, or 2 mm or more. Further, the thickness of the intermediate glass layer is not critical. However, it may preferably be in the range of from about 20 to 100 $\mu$m. The advantages brought about by the increase in thickness of the glass-hydroxyapatite ceramic layer are as follows. In conducting an implantation, the preparatory treatment of the human bone is facile because the size of a hole of bone to receive the implant does not need to be strictly controlled. The reason for this is that it is possible to readily produce an implant having any desired thickness according to the present invention. Further, the life of a thick layer would be longer, although it is known that any implant would slowly and constantly eroded through biochemical reactions in the human body. Furthermore, according to the present invention, the surface state of the implant can be freely controlled by changing the HAP particle size or etching time, etc., so as to be suitable for any implant site of a human body. In many cases, thicker layers are suitable for intricate treatment.

The composite material of the present invention is strong because of the use of a substrate having excellent mechanical strength and chemical resistance in the composite material. Such use increases the mechanical strength of the composite material as a whole. Further, the composite material of the present invention can be readily bonded to the bone in vivo because a vast plurality of voids which facilitate bone ingrowth into the surface portion of the composite material are present on the surface portion of the composite material and because the hydroxyapatite ceramic, being comprised mainly of HAP which has bioactivities, is exposed. Moreover, the composite material of the present invention can maintain the desired bioactivities for a prolonged period of time because the hydroxyapatite ceramic which exhibits such desired bioactivities is firmly held in the continuous glass phase and, hence, is prevented from dissolving out into body. In addition, in the present invention, an intermediate layer comprised of glass may be provided between the substrate and the glass-hydroxyapatite ceramic layer. The provision of the intermediate layer is preferred because it increases the strength of adhesion between the substrate and the glass-hydroxyapatite layer and because it enables the content of the hydroxyapatite ceramic of the glass-hydroxyapatite ceramic layer to be widely varied, leading to the biocompatible composite material having a wide variety of applications.

The present invention will now be described in detail with reference to the following Examples, which should not construed to be limiting the scope of the present invention.

EXAMPLE 1

An alumina borosilicate glass having the same composition as that of Sample No. 1 described in Table 1 mentioned before was heated up to 800° C. over 1 hour in an electric furnace, and then maintained at 800° C. for 1 hour. Further, the glass was heated up to 1400° C. over 1.5 hours in the electric furnace and then maintained at 1400° C. for 1.5 hours, followed by rapid cooling in water, thereby to obtain a glass frit. Then, the thus obtained glass frit was dried and pulverized by means of a pot mill made of alumina for 36 hours, followed by sifting by means of a sieve of 200 mesh (Tyler), thereby to prepare a powdery glass having a particle size of 74 $\mu$m or less.

On the other hand, 37 g of a commercially available $Ca(OH)_2$ of guaranteed reagent class was dissolved in 600 ml of water to prepare an aqueous $Ca(OH)_2$ solution having a pH of 12 to 13. Then, according to the wet method mentioned before, HAP was prepared as follows. 15 w/v % aqueous $H_3PO_4$ solution was dropwise added to the above-obtained aqueous $Ca(OH)_2$ solution, while stirring the $Ca(OH)_2$ solution with a magnetic stirrer at 40° C. and maintaining the pH value of the system at higher than 7.0, to form a precipitate. The precipitate was sufficiently washed with water and then dried at 110° C. for 16 hours. The dry precipitate was calcined at 800° C. and subsequently at 1200° C., thereby to obtain HAP. Further, from the thus obtained HAP, a powdery HAP having a particle size of 74 $\mu$m or less was prepared by sifting by mean of a sieve of 200 mesh (Tyler).

Then, the powdery HAP and glass which were obtained above were mixed so that the weight ratios of the HAP to the glass became 10:90, 30:70, 50:50 and 70:30, respectively, to prepare four HAP-glass mixtures.

On the other hand, titanium substrates were subjected to degreasing using trichloroethylene and then washed with $HNO_3$ or a mixture (1:1 by volume) of HF and $HNO_3$, followed by blast treatment with alundum to prepare titanium (Ti) substrates having an average roughness of 2.3–6.8 $\mu$m. On the other hand, blast-treated Ti substrates were prepared in substantially the same manner as mentioned just above and subjected to heat treatment at 950° C. for 10 min in vacuo to form an oxide layer on the surfaces of the titanium substrates.

Then the HAP-glass mixtures obtained above were separately pressed by means of a molding machine to prepare four kinds of tablets having a diameter of 1.5 cm and a thickness of 0.5 mm. The tablets were separately fired at 950° C. to 1050° C. The surfaces of the tablets were examined by means of an electron probe microanalyzer (EPMA) to obtain SE images. The SE images are shown in FIGS. 2 (a) to (d). In FIGS. 2 (a) to (d), the HAP contents of the tablets are (a) 10 wt %, (b) 30 wt %, (c) 50 wt % and (d) 70 wt %, respectively.

On the other hand, an HAP-glass mixture containing 30 wt % HAP was prepared in the same manner as mentioned above. Then, a tablet of the mixture was prepared in substantially the same manner as described above except that the firing temperature and time were 900° C. and 5 min, respectively. The above-obtained tablet was etched using 10% w/v aqueous HF solution for 30 min, thereby to obtain a glass-HAP ceramic tablet. In the surface portion of the tablet, there were uniformly dispersed fine crystals of HAP and there were numerous continuous voids and cracks. FIG. 3 (a) shows an SE image of the etched surface portion of the glass-HAP ceramic tablet. FIG. 3 (b) shows an SE image of a cross section of the etched surface portion of the tablet. As is seen from FIG. 3 (b), HAP is present at a high concentration in the surface portion. FIG. 3 (c) shows an SE image of another cross section of the tablet, showing the interior portion of the tablet. As is apparent from FIG. 3 (c), in the interior portion of the tablet, HAP was dispersed in the form of aggregates having various sizes.

Furthermore, using a glass-HAP mixture containing 30 wt % HAP, two glass-HAP ceramic tablets were prepared in substantially the same manner as described above except that the firing temperature and time were 900° C. and 3 min, respectively. Then, the tablets were etched using 10 w/v % aqueous HF solution and a mixture (1:1 by volume) of 8 w/v % HF and 15 w/v % HNO$_3$, respectively. Thus, there were obtained glass-HAP ceramic tablets In the etched surface portions of the tablets, there were uniformly dispersed fine crystals of HAP and there were numerous continuous voids and cracks. FIGS. 4 (a) and (b) are SE images of the etched surface portions of the tablets, which have been etched for 3 min using 10 w/v % HF and etched for 3 min using a mixture (1:1 by volume) of 8 w/v % HF and 15 w/v % HNO$_3$, respectively. As is apparent from FIG. 4 (a) and (b), in the etched surface portions of the tablets, HAP was non-uniformly dispersed. Further, the surface portion had an extremely rough structure and numerous microcracks having a width in the order of μm and voids of about several microns in diameter were formed. Such a structure is advantageous for coaptation with an osseous tissue.

Next, a blend of a powdery glass with hydroxyapatite, of which the HAP content was 50% by weight, was prepared in the same manner as mentioned above. The blend was applied to the surface of the above-obtained titanium substrate to form a coated substrate so that the thickness of the coat layer became about 100 μm. The coated substrate was fired at a temperature within 850° to 950° C. to obtain a preliminary product comprising the titanium substrate having a glass-HAP ceramic layer formed thereon. The surface of the preliminary product was observed by means of a scanning electron microscope (SEM). Then the preliminary product was etched using a 1:1 by volume mixture of 8 w/v % HF and w/v % HNO$_3$ for 10 min to obtain a composite material of the present invention. Incidentally, after 3, 5 and 10 minutes from the initiation of etching, the surface portion of the product was observed by means of an SEM. The SEM photographs of the surface portions of the non-etched preliminary product and the etched product are shown in FIGS. 5 (a) to (e). FIG. 5 (a) is the SEM photograph of the non-etched product. FIGS. 5 (b) to (d) are those of the products etched for 3, 5 and 10 min, respectively. FIG. 5 (e) is a magnification (×2.5) of FIG. 5 (d). In each of FIGS. 5 (a) to (e), the length of the scale represents 20 μm.

On the other hand, two blends of a powdery glass with HAP, of which the HAP contents were 30% and 50% by weight, respectively, were prepared in substantially the same manner as mentioned above. The blends were fired at 950° C. separately. Separately, a powdery glass was also fired at 950° C. Then, those fired samples were subjected to X-ray diffractometry and differential scanning calorimetry (DSC) to obtain X-ray diffraction patterns and DSC curves of the samples. From the comparison of the X-ray diffraction patterns and DSC curves of the fired glass-HAP samples with those of the fired glass samples, it was confirmed that HAP did not react with the glass.

EXAMPLE 2

Figures 6A, 6B:
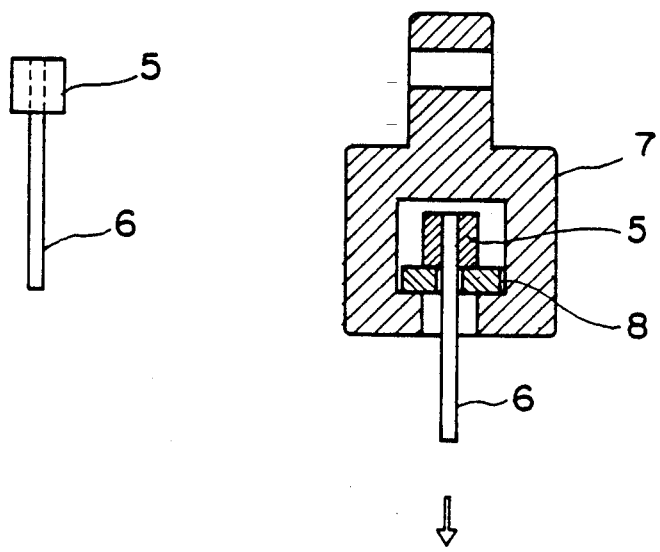
FIG. 6 (a) is a diagrammatic cross section of a sample composite material used for measuring the pull out strength of a biocompatible composite material.

A powdery glass was prepared in substantially the same manner as described in Example 1. Then, the powdery glass and a Ti rod having a diameter of 3.1 mm, a length of 50 mm and a surface average roughness within the range of from 0.2 to 6.8 μm were set in a carbon die so that a joint between the glass powder and the Ti rod became 10 mm×10 mm, and sintering was effected at 900° C. for 5 min in an atmosphere of air, to form a glass-titanium composite. Substantially the same procedure as mentioned above was repeated except that titanium rods having various surface average roughnesses in the range of from 0.2 to 6.8 μm were used, to obtain glass-titanium composites. Each of the glass-titanium composites was used as a sample for the measurement of a pull out strength FIG. 6 (a) is a diagrammatic cross section of a sample for the measurement of a pull out strength. In FIG. 6 (a), numerals 5 and 6 designate a glass portion and a Ti rod portion, respectively. The pull out strength of the sample was determined using a testing machine, model 1125 (manufactured and sold by Instron Co., U.S.A.) as follows. In FIG. 6 (b), numeral 7 designates a supporting tool 7. A load cell (not shown) is provided above the supporting tool 7. The Ti rod 6 of the sample was pulled in the direction of an arrow so that the pulling force was applied to the Ti rod 6 and the glass portion 5 through a spacer 8. The pulling rate was increased at a rate of 1 mm/min to increase the pulling force until the Ti rod was pulled out of the glass portion. A load at which the Ti rod 6 was pulled out of the glass portion 5 was measured by means of the load cell to determine the pull out strength of the sample. The pull out strength of the sample corresponds to the joint strength between the Ti rod and the glass of the sample.

The measurement of a pull out strength was conducted using samples prepared in substantially the same manner as mentioned above except that the sintering temperature and time were 1050° C. and 20 min, respectively.

Figure 8:
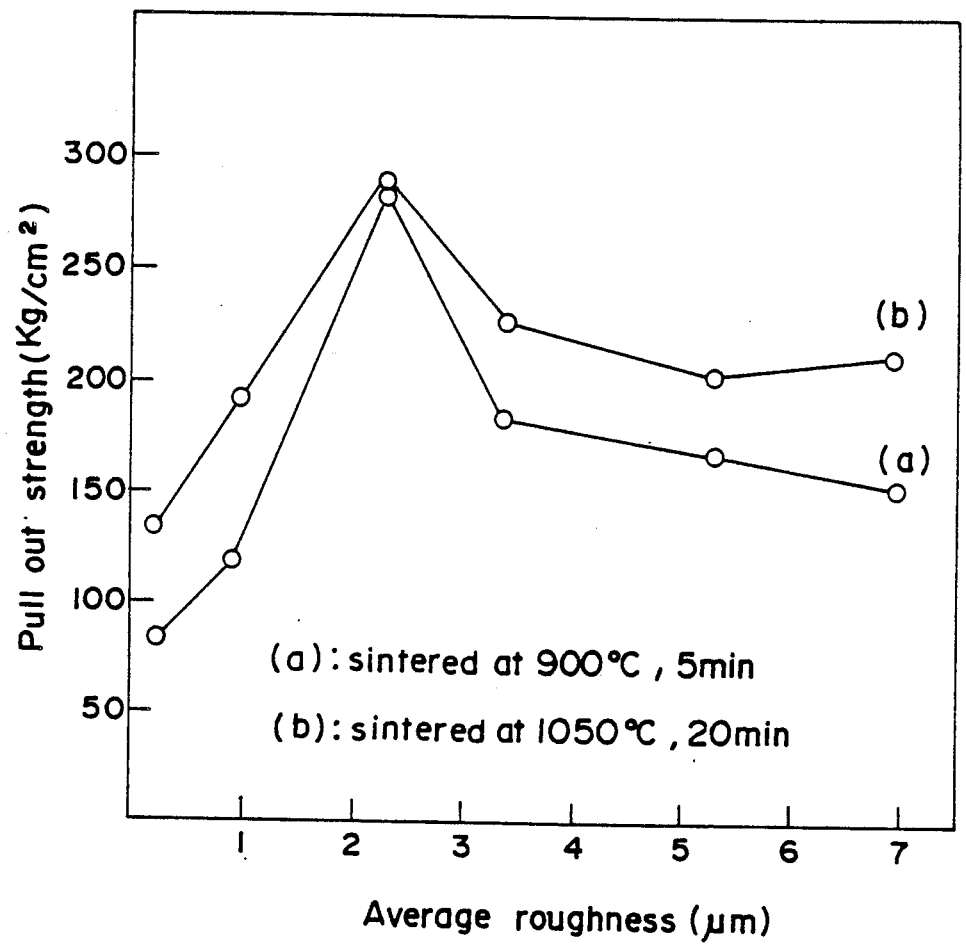
FIG. 8 is a graph showing the relationships between the pull out strength and the average roughness of the surface of a biocompatible composite material.

The results of the above-mentioned measurements are shown in FIG. 8. In FIG. 8, the relationships between the pull out strengths of the samples and the average roughnesses of the surface of the Ti rod are shown.

On the other hand, blends of a powdery glass with an HAP ceramic which have various HAP contents of from 0% to 90% by weight, were prepared in substantially the same manner as described in Example 1. Then, each of those blends and a Ti rod having a diameter of 3.1 mm, a length of 50 mm and a surface average roughness of 3.4 μm were set in the same carbon die as mentioned above, and sintered at 900° C. for 5 min in an atmosphere of air, thereby to form a glass-HAP layer-titanium composite material. The glass-HAP layer-titanium composite material was used as a sample for the measurement of a pull out strength. The structure of the sample was substantially the same as illustrated in FIG. 6 (a). Then, the pull out strength of the sample was determined in substantially the same manner as described above.

Figure 7:
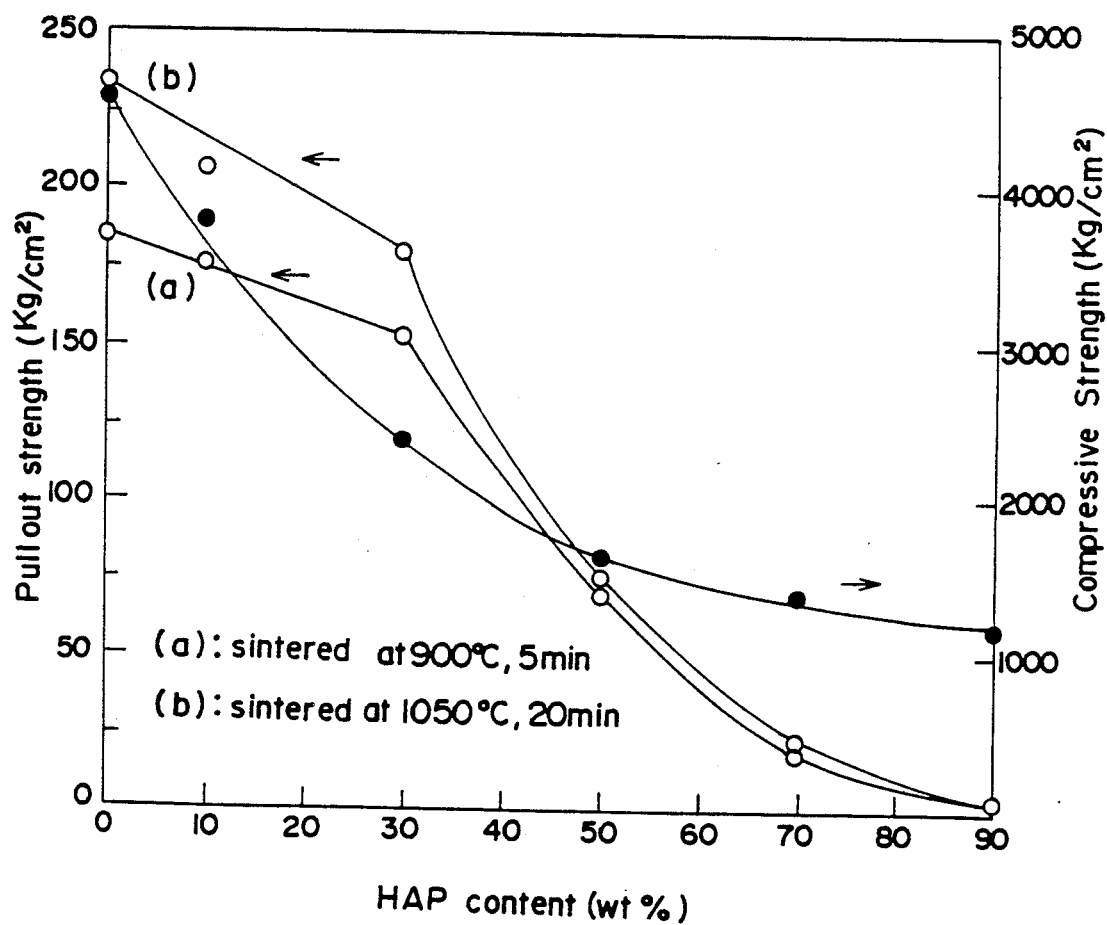
FIG. 7 is a graph showing the relationships between the pull out strength and the HAP content of the glass-HAP ceramic layer of a biocompatible composite material and between the compressive strength and the HAP content.

On the other hand, glass-HAP layer-titanium composite materials were also formed in substantially the same manner as described above except that the sintering temperature and time were 1050° C. and 20 min, respectively. The pull out strength of each of the glass-HAP layer-titanium composite materials was determined in substantially the same manner as described above. The results of the measurements are shown in FIG. 7. In FIG. 7, the relationship between the pull out strength of the glass-HAP layer-titanium composite material and the HAP content (wt %) thereof is shown.

In addition to the measurement of the pull out strength of the composite material, the compression strength of the composite material was measured as follows. Blends of a powdery glass with an HAP which have various HAP contents as shown in FIG. 8 were separately sintered in a carbon die at 950° C. to form tablets having a diameter of 5 mm and thickness of 5 mm. Then, each of the tablets was set in the testing machine as used in the measurement of the pull out strength mentioned above, and was pressed. A load at which the tablet was crushed was measured by means of the load cell mentioned above. The results are also shown in FIG. 7, in which the relationship between the compressive strength and the HAP content is shown by filled circles. As is apparent from FIG. 7, the compression strength of the glass-HAP ceramic composition decreases according to the increase of HAP content in the glass-HAP ceramic composition.

Next, to the surface of a titanium substrate having a rod shape (4 mm$\phi$ × 25 mm) was applied a glass as used in Example 1 so that the thickness of the resulting glass layer on the surface of the titanium rod became about 60 $\mu$m. Then, to the surface of the resulting substrate having the glass layer thereon was applied a blend of a glass as used in Example 1 with HAP which had a HAP content of 60% by weight so that the thickness of the resulting blend layer became about 130 $\mu$m. The resulting coated substrate was fired at 950° C. for 5 to 10 min in an atmosphere of air, to obtain a biocompatible composite material (A).

Substantially the same procedure as mentioned above was repeated except that the HAP content was changed, to obtain biocompatible composite materials respectively having various HAP contents, to 90% by weight, including a biocompatible composite material (B) having an HAP content of 30% by weight and a composite material (C) having an HAP content of 0.

Further, substantially the same procedure as mentioned above was repeated except that a Ti-6Al-4V alloy rod was used as a substrate instead of the titanium rod, to obtain biocompatible composite materials.

With respect to the composite material having the glass layer prepared by heating at 950° C. for 5 min, there was observed no oxide layer between the glass layer and the Ti substrate.

In the above-mentioned sample composite materials, the strength of adhesion between the substrate and the glass-HAP ceramic layer changed according to the average roughness of the surface of the Ti substrate as shown in FIG. 8, and an average roughness of 2.3 $\mu$m gave the largest value, 285 Kg/cm². The pull out strength of the composite material is decreased with the increase in the HAP content of the glass-HAP ceramic layer as shown in FIG. 7 (e.g. when the HAP content is 30%, the strengths of adhesion are 160 Kg/cm² and 180 Kg/cm² with respect to the composite materials sintered at 900° C. for 5 min and at 1050° C. for 20 min, respectively). However, by employing a glass layer between the glass-HAP ceramic layer and the Ti substrate, the strength of adhesion could be retained. A clear boundary was not observed between the glass-HAP ceramic layer and the intermediate glass layer since both the layers had completely fused with each other. Further, the HAP ceramic particles were uniformly dispersed in the glass-HAP ceramic layer. On the other hand, with respect to the glass-HAP layer-titanium composite material prepared by heating at 1050° C. for 20 min, an oxide layer was formed at the interface on the Ti substrate surface and the intermediate glass layer, and at a portion adjacent the oxide layer on the side of the intermediate glass layer there was observed the formation of $Ti_5Si_3$. The oxide layer formed between the intermediate glass layer and the Ti substrate increases the strength of adhesion therebetween.

Each composite material as obtained above was implanted in a pig femur and 2 months later, the pig femur was excised and observed by means of EPMA. It was found that the coaptation between the glass-HAP composite material and bone was extremely excellent [see FIGS. 1 and 9 (b) and 10 (b)].

Figure 10A:
FIG. 10 (b) is an SE image of a cross section of a system comprising a cancellous bone of a pig femur and, implanted therein, a composite material comprising a titanium substrate having a glass layer formed thereon after 2 months from the implantation.

For comparison, the above-obtained composite material (C) was implanted in a pig femur. 2 months later, the pig femur was excised and the bonding characteristic between the composite material (C) and the bone was observed. The results are shown in FIGS. 9(a) and 10(a).

Figure 1:
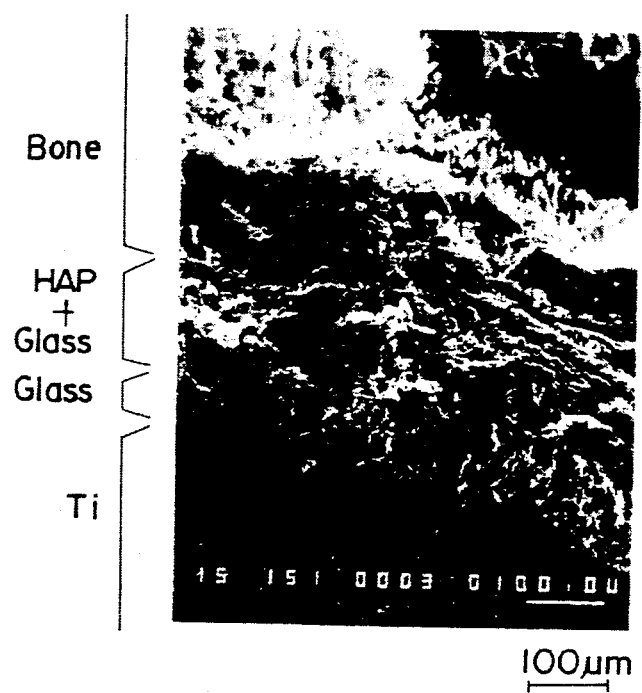
FIG. 1 is a secondary electron image (hereinafter often referred to as "SE image") showing the interface between a biocompatible composite material of the present invention and a cortical bone of a pig femur after 2 months from the implantation of the composite material in a pig femur.

FIG. 1 is an SE image showing the interface between the above-obtained composite material (A) and the bone after two months from the implantation. The HAP content of the glass-HAP ceramic layer was 60% by weight as mentioned above. The EDX (Energy Diffusion X-ray) analysis of the composite material of FIG. 1 showed that a portion indicated by numeral 1 contained Si, a portion indicated by numeral 2 contained Si, Ca and P in amount proportions represented by Si>Ca>P, a portion indicated by numeral 3 contained Ca, P, Si and Al in amount proportions represented by Ca>P>Si>Al, and a portion indicated by numeral 4 contained Ca and P in amount proportions represented by Ca>P. From the results, it is apparent that the portion indicated by numeral 1 is the glass layer, the portion indicated by numeral 2 is the interface between the glass layer and the glass-HAP ceramic layer, the portion indicated by numeral 3 is the interface between the glass-HAP ceramic layer and the bone, and the portion indicated by numeral 4 is the bone. In FIG. 1, the interface between the glass-HAP ceramic layer and the bone was hardly recognized. This indicates that the layer and the bone are well coapted to each other.

FIG. 9 (a) and (b) are SE images respectively showing the interfaces between the bone and the composite material (comparative) composed of a titanium substrate and only a glass layer formed thereon, and the interface between the bone and the above-obtained composite material (B) of the present invention comprised of a titanium substrate having a glass-HAP ceramic layer formed thereon through the intermediate glass layer. With respect to the comparative composite material, as is apparent from FIG. 9 (a), there was recognized a gap between the glass layer and the cortical bone of the pig femur. In contrast, with respect to the composite material (B) of the present invention, as is apparent from FIG. 9 (b), the coaptation between the glass-HAP ceramic layer and the bone was excellent and, therefore, the boundary between the glass-HAP ceramic layer and the tissues of the bone was hardly recognized. This indicates that the glass-HAP ceramic layer of the present composite material and the tissue of the bone were well coapted to each other.

Figure 10B:
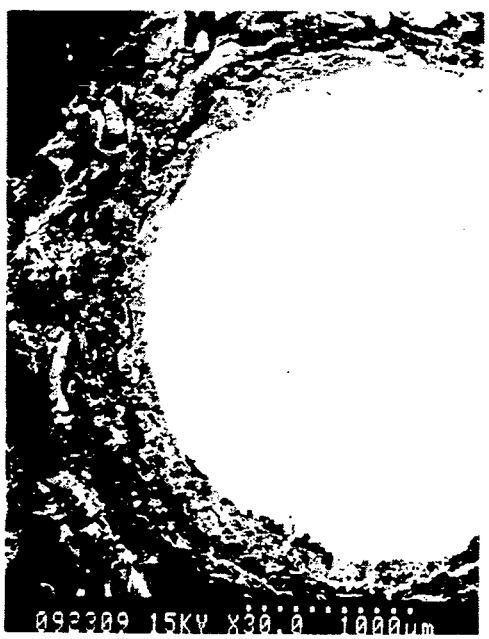

FIG. 10 (a) is an SE image of the cross section of a system comprising a cancellous bone of a pig femur and, implanted therein, a composite material (comparative) comprising a titanium substrate having only a glass layer formed thereon, and FIG. 10 (b) is an SE image of a cross section of a system comprising a cancellous bone of a pig femur and, implanted therein, the biocompatible composite material (A) (present invention). The SE images ere obtained after 2 months from the implantation. As is apparent from FIGS. 10 (a) and (b), the coaptation between the bone and the biocompatible composite material of the present invention was excellent [FIG. 10 (b)], whereas the comparative composite material was not coapted to the bone, leaving a gap between the composite material and the bone [FIG. 10 (a)].

EXAMPLE 3

508 A powdery glass was prepared in the same manner as in Example 1. Separately, two different blends of a powdery glass with HAP were also prepared in the same manner as in Example 1 except that the HAP contents of the blends were 20% and 60% by weight, respectively.

To the surface of a titanium rod of 2.2 mm$\phi$ × 10 mm in size was applied the above-obtained powdery glass in a thickness of about 30 μm, dried at 100° C. for 20 min and then fired at 950° C. for 5 min in an electric furnace. Thus, there was obtained a semi-coated substrate.

Next, to the surface of the above-obtained semi-coated substrate was applied the above-obtained glass-HAP blend having an HAP content of 20% by weight in a thickness of about 40 μm and dried at 100° C. for 20 min, followed by firing at 950° C. for 5 min in an electric furnace, thereby to obtain a coated substrate.

Then, to the surface of the above-obtained coated substrate was further applied the above-obtained glass-HAP blend having an HAP content of 60% by weight in a thickness of about 100 μm, dried at 100° C. for 20 min and then fired at 950° C. for 5 min in an electric furnace to obtain a further coated substrate.

The thus obtained further coated substrate was etched using a 1:1 by volume mixture of 5 w/v % HF and 10 w/v % HNO$_3$ for 5 min to obtain a biocompatible composite material.

Figures 11A, 11B, 11C:
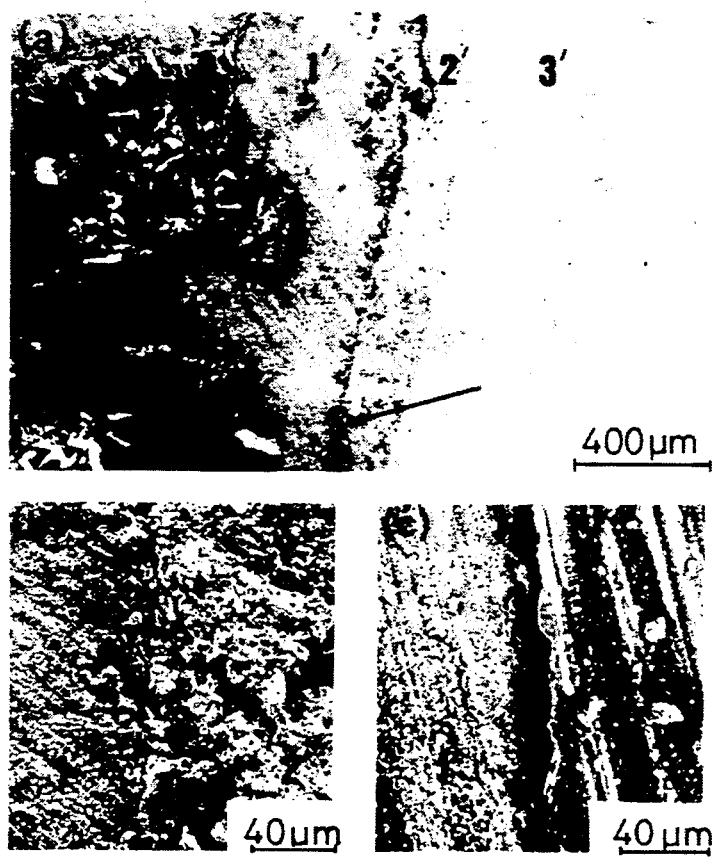
FIG. 11 (a) is an SEM photograph of a cross section of the interface between a cortical bone of a dog mandible and a biocompatible composite material of the present invention after 2 months from the implantation of the composite material in a dog mandibular bone.

Then, the thus obtained biocompatible composite material was implanted in a mandibular bone of a dog. As the dog, there was used a dog of which the 2nd, 3rd and 4th premolars in the mandibular bone had been extracted and their wounds had been healed over 10 weeks. After 2 months from the implantation, the mandibular bone was excised and the biological bonding characteristic was observed by means of SEM. The results are shown in FIG. 11 (a) and (b), in which numerals 1', 2', and 3' designate portions respectively of the bone, glass-HAP ceramic layer and titanium substrate. As is apparent from FIG. 11 (a) and (b), the surface structure of the above-mentioned biocompatible composite material was well suited for fresh bone to ingrow histologically. That is, osseointegration of the interface between the implanted composite material and the alveolar/cancellous bone was observed within 2 months after the implantation.

For comparison, a titanium rod was implanted in a mandibular bone of a dog in substantially the same manner as mentioned above and 2 months later, the mandibular bone was excised and observed by means of SEM. The result is shown in FIG. 11 (c), in which numerals 1' and 3' indicate portions respectively of the bone and titanium substrate. As is apparent from the result, a gap was clearly observed between the titanium rod and the bone.

EXAMPLE 4

A titanium substrate having a rod shape (4 mm$\phi$ × 25 mm) was pickled with a 1:1 by volume mixture of 8 w/v % HF and 15 w/v % HNO$_3$ and then subjected to blasting with an alundum so that the average roughness of the surface thereof became 3.4 μm. Separately, a powdery glass was prepared in the same manner as in Example 1.

To the surface of the above-obtained titanium substrate was applied the above-obtained powdery glass in a thickness of about 50 μm, dried at 100° C. for 20 min and then fired at 950° C. for 5 min in an electric furnace. Thus, there was obtained a semi-coated substrate.

Next, to the surface of the above-obtained semi-coated substrate was applied a glass-HAP blend having a HAP content of 20% by weight in a thickness of about 50 μm and dried at 100° C. for 20 min, followed by firing at 950° C. for 5 min in an electric furnace, thereby to obtain a coated substrate.

Then, to the surface of the above-obtained coated substrate was further applied a glass-HAP blend having an HAP content of 40% by weight in a thickness of about 50 μm, dried at 100° C. for 20 min and then fired at 950° C. for 5 min in an electric furnace to obtain a further coated substrate.

Then, to the surface of the above-obtained further coated substrate was still further applied a glass-HAP blend having an HAP content of 60% by weight in a thickness of about 50 μm, dried at 100° C. for 20 min and then fired at 950° C. for 5 min in an electric furnace to obtain a still further coated substrate. Then, the same procedure as mentioned just above for the formation of a glass-HAP layer having a HAP content of 60% by weight, was repeated once more.

Then, to the surface of the above-obtained further coated substrate was still further applied a glass-HAP blend having an HAP content of 80% by weight in a thickness of about 50 μm, dried at 100° C. for 20 min and then fired at 900° C. for 5 min in an electric furnace to obtain a still further coated substrate.

Then, to the surface of the above-obtained further coated substrate was still further applied a glass-HAP blend having an HAP content of 90% by weight in a thickness of about 50 μm, dried at 100° C. for 20 min and then fired at 900° C. for 5 min, followed by etching by a mixture (1:1 by volume) of 3 w/v % HF and 7 w/v % HNO$_3$ for 5 min, thereby to obtain a composite material, of which the glass-HAP ceramic layer was comprised of 7 sub-layers, of which the fourth and fifth sub-layers had the same HAP content.

What is claimed is:

1. A biocompatible composite material comprising a substrate having an inorganic glass-hydroxyapatite ceramic layer disposed thereon directly or through an intermediate layer, said intermediate layer consisting essentially of an inorganic glass being bonded to each of the opposing surfaces of the substrate and the inorganic glass-hydroxyapatite ceramic layer;

said inorganic glass-hydroxyapatite ceramic layer consisting essentially of a continuous inorganic glass phase having a hydroxyapatite ceramic dispersed therein, said hydroxyapatite ceramic having a calcium/phosphorus molar ratio of 1.50 to 1.75, wherein said hydroxyapatite ceramic consists essentially of hydroxyapatite, and wherein the surface portion of said glass-hydroxyapatite ceramic layer is in a roughened state having voids and having the hydroxyapatite ceramic of the glass-hydroxyapatite ceramic layer exposed;

said glass-hydroxyapatite ceramic layer having an inorganic glass content of from 50 to 85% by weight when the inorganic glass-hydroxyapatite ceramic layer is directly disposed on the substrate;

said inorganic glass-hydroxyapatite ceramic layer having a glass content of from 30 to 85% by weight when the inorganic glass-hydroxyapatite ceramic layer is disposed on the substrate through said intermediate layer;

said inorganic glass being selected from the group consisting of an alumina borosilicate glass and an aluminosilicate glass, said alumina borosilicate glass containing 75 to 85% by weight of a mixture of $SiO_2$, $B_2O_3$ and $Al_2O_3$, based on the weight of the glass, and 14 to 20% by weight of at least one alkali metal oxide and/or at least one alkaline earth metal oxide, based on the weight of the glass, said alumino-silicate glass containing 60 to 75% by weight of a mixture of $SiO_2$ and $Al_2O_3$, based on the weight of the glass, and 14 to 20% by weight of at least one alkali metal oxide and/or at least one alkaline earth metal oxide, based on the weight of the glass.

2. The composite material according to claim 1, wherein said glass-hydroxyapatite ceramic layer comprises a plurality of sub-layers each comprising a continuous glass phase having a hydroxyapatite ceramic dispersed therein, said sub-layers having different hydroxyapatite ceramic contents which are increased from the innermost sub-layer toward the outermost sub-layer, and wherein the surface portion of the outermost sub-layer of said glass-hydroxyapatite ceramic layer is in a roughened state having voids and having the hydroxyapatite ceramic of the glass-hydroxyapatite ceramic layer exposed.

3. The composite material according to claim 1, wherein said glass-hydroxyapatite ceramic layer comprises at least three sub-layers each comprising a continuous glass phase having a hydroxyapatite ceramic dispersed therein, said sub-layers including at least one combination of at least two mutually adjacent sub-layers of which the hydroxyapatite ceramic contents are identical with each other and having different hydroxyapatite ceramic contents between at least two mutually adjacent sub-layers, in which the hydroxyapatite ceramic contents of the sub-layers constituting the entire glass-hydroxyapatite ceramic layer are increased from the innermost sub-layer toward the outermost sub-layer through at least one sub-layer of which the hydroxyapatite ceramic content is identical with that of a sub-layer immediately preceding said sub-layer, and wherein the surface portion of the outermost sub-layer of said glass-hydroxyapatite ceramic layer is in a roughened state having voids and having the hydroxyapatite ceramic of the glass-hydroxyapatite ceramic layer exposed.

4. The composite material according to claim 1, 2 or 3, wherein said glass of the glass-hydroxyapatite ceramic layer comprises a borosilicate glass or an aluminosilicate glass.

5. The composite material according to claim 4, wherein said borosilicate glass comprises from 75 to 85% by weight of a mixture of $SiO_2$, $B_2O_3$ and $Al_2O_2$, based on the weight of the glass, and from 14 to 20% by weight, based on the weight of the glass, of at least one metal oxide, in which the metal of the metal oxide is a member selected from the group consisting of an alkali metal and an alkaline earth metal.

6. The composite material according to claim 4, wherein said aluminosilicate glass comprises from 60 to 75% by weight of a mixture of $SiO_2$ and $Al_2O_3$, based on the weight of the glass, and from 14 to 20% by weight, based on the weight of the glass, of at least one metal oxide in which the metal of the metal oxide is a member selected from the group consisting of an alkali metal and an alkaline earth metal.

7. The composite material according to any one of claim 1 to 3, wherein said substrate is selected from the group consisting of a metallic substrate and a ceramic substrate.

8. The composite material according to claim 7, wherein said substrate is a metallic substrate.

9. The composite material according to claim 8, wherein said metallic substrate comprises Ti or a Ti alloy.

10. The composite material according to claim 9, wherein said Ti alloy comprises Ti and Al.

11. The composite material according to claim 8, wherein said glass of the glass-hydroxyapatite ceramic layer has a linear thermal expansion coefficient which corresponds to from about 80 to 95% of that of the metallic substrate.

12. The composite material according to claim 11, wherein said glass of the glass-hydroxyapatite ceramic layer has a linear thermal expansion coefficient which corresponds to from about 90 to about 95% of that of the metallic substrate.

13. The composite material according to claim 8, wherein said glass of the intermediate layer has a linear thermal expansion coefficient which corresponds to from about 80 to 95% of that of the metallic substrate.

14. The composite material according to claim 13, wherein said glass of the intermediate layer has a linear thermal expansion coefficient which corresponds to from about 90 to about 95% of that of the metallic substrate.

* * * * *